United States Patent [19]

Creekmore

[11] Patent Number: 4,582,487
[45] Date of Patent: Apr. 15, 1986

[54] LINGUAL ORTHODONTIC APPLIANCE SYSTEM FOR EDGEWISE THERAPY

[75] Inventor: Thomas D. Creekmore, 1620 Fountainview, Houston, Tex. 77057

[73] Assignee: Thomas D. Creekmore, Houston, Tex.

[21] Appl. No.: 594,800

[22] Filed: Mar. 29, 1984

[51] Int. Cl.$^4$ ............................................. A61C 7/00
[52] U.S. Cl. ............................................. 433/8; 433/9
[58] Field of Search ...................................... 433/8, 9

[56] References Cited

U.S. PATENT DOCUMENTS

3,930,311  1/1976  Andrews ............................. 433/15
4,337,037  6/1982  Kurz ................................... 433/9

Primary Examiner—Robert Peshock
Attorney, Agent, or Firm—Gunn, Lee & Jackson

[57] ABSTRACT

A lingual orthodontic appliance system for edgewise orthodontic therapy incorporating twin type brackets with single bracket interbracket width. Brackets for anterior teeth incorporate three tie wings in T-shaped orientation and brackets for bicuspids have two pairs of twin tie wings. Molar tube brackets retain the terminal extremities of the archwire and provide hooks for closing loops, tie-back loops, etc. In each case the archwire slot opens toward the occlusal permitting simple and efficient insertion and positioning of the archwire within the various brackets of the appliance system.

20 Claims, 14 Drawing Figures

LINGUAL ORTHODONTIC APPLIANCE SYSTEM FOR EDGEWISE THERAPY

FIELD OF THE INVENTION

This invention relates generally to orthodontic brackets which are utilized by orthodontists to accomplish accurate movement and positioning of the teeth of a patient. More specifically, the present invention concerns the provision of a lingual orthodontic bracket system which may be utilized to permit the labial and buccal surfaces of the teeth to be free of orthodontic applicances to thus retain a pleasing appearance during the period of orthodontic therapy. Even further, this invention concerns the provision of a lingual orthodontic bracket system which permits orthodontists to impart forces directly to the lingual surfaces of a patient's teeth in order to accomplish desirable tooth movement.

RELATED INVENTION

This invention is related to the subject matter of U.S. patent application Ser. No. 369,932, filed Apr. 19, 1982, behalf of Thomas D. Creekmore and entitled Lingual Orthodontic Appliance System for Edgewise Therapy.

BACKGROUND OF THE INVENTION

Although a number of differing orthodontic techniques exist, the majority of orthodontists in practice in the United States, at the present time, utilize one of two basic techniques of orthodontic therapy in their treatment of patients. These basic techniques are the "light-wire" technique and the "edgewise" technique. Light-wire appliances were first designed and presented to the profession by an Australian orthodontist, R. P. Begg, who introduced the idea of differential force control. Since some types of tooth movements evoke more tissue resistance than others, and some movements occur faster than others, Begg reasoned that by selectively choosing the movements required and relating the reciprocal reactions properly, tooth movement might be accomplished in orderly manner. The Begg light-wire technique is characterized by a number of significant features. Brackets are fixed to all of the teeth of the patient anterior to and including the first molars. Archwires are round in cross-section and provide archform and leveling of the teeth. Archwires are loosely pinned to the bracket and are not ligated. The Begg brackets provide a single point contact with the archwire to minimize friction and permit the teeth to slide, rotate, tip and torque freely. Tip, torque and rotation are accomplished by auxiliaries and not by the active fit between the archwire and bracket as in the edgewise technique. Extra oral anchorage is not used. Reciprocal anchorage is provided for by selectively utilizing teeth posterior to extraction sites to retract teeth anterior to the extraction sites with intra and inter maxillary elastics. The light-wire appliances are now several and varied from the original design, although all employ sophisticated concepts in theories of tooth movement and anchorage control. Standard light-wire therapy does not utilize extra-oral traction, frequently involves extraction of teeth and typically employs more auxiliaries than conventional edgewise therapy.

The most widely utilized orthodontic therapy technique in this country, and the technique to which this invention is directed, is the "edgewise" technique, which was brought to the industry by Dr. Edward H. Angle. It should be understood, however, that this invention is also applicable to other orthodontic techniques such as the multi-phase and twin wire techniques, for example. In the beginning stages of edgewise therapy, archwires of circular cross-sectional configuration are employed. The greater flexibility of the round wire used in initial edgewise therapy permits greater range of movement of malposed teeth with less force to the teeth. For secondary and finishing therapy, the edgewise technique typically incorporates a multi-banded precision appliance consisting of a labial archwire of rectangular cross-section configuration that is ordinarily of greater dimension at the sides than at the edges thereof. The archwire is fitted and ligated with metal ligature wire, or ligature elastics, or any other suitable form of mechanical retention, into precision mating horizontal archwire slots that are formed in brackets on all of the permanent teeth including first molars and frequently second molars. The archwire terminates in buccal tubes each having a rectangular passage through which the end portions of the rectangular archwire extend. The archwire, which may be composed of stainless steel or precious alloy, is typically positioned with its narrow dimension or edge lying against the labial and buccal surfaces of the teeth. This feature gives the technique its name "edgewise." The edgewise technique makes control possible in all directions and any individual tooth may be moved simultaneously in three directions; for example, an incisor may be moved lingually, distally and rotated around its long axis with one adjustment of the archwire. The rectangular cross-sectional configuration of the edgewise archwire permits it to be twisted to a desired extent and, being of spring-like nature, the twisting forces will be applied through the archwire to the teeth, thereby inducing a torquing movement of the teeth as the archwire becomes untwisted and returns to its normal configuration. The brackets are precision milled to define archwire slots of rectangular shape so that the orthodontist can select precision milled archwires to fit as precisely as desired. Tip, torque and rotation are accomplished by the fit between the archwire and the bracket. Extra oral anchorage may or may not be used as desired. Reciprocal anchorage can be provided by extraction of teeth and selectively utilizing teeth posterior to extraction sites to retract teeth anterior to the extraction sites with intra and inter maxillary elastics and/or closing loop archwires. This invention is generally directed to the edgewise technique as applied lingually to the teeth and concerns an orthodontic appliance system that integrates specific advantages that are afforded by edgewise appliances with both single and twin ligating tie wings.

As mentioned above, conventional edgewise therapy is typically accomplished by means of a labial archwire that is received by precision archwire slots formed by orthodontic brackets that are positioned at the labial surfaces of a patient's teeth. In many cases, undesirable psychological phenomena occurs since the appearance of a patient's teeth might be considered unpleasant, especially by the patient, because of the presence of orthodontic appliances on the labial and buccal surfaces of the teeth. Suppliers of orthodontic appliances, to provide for more aesthetically pleasing therapy, have in some cases eliminated the metal bands that typically encircle the teeth and have developed brackets that are adapted for direct bonding to the enamel surfaces of the teeth. Still, with the archwire present at the labial and buccal surfaces of the patient's teeth, it is not possible to provide the patient with an orthodontic appliance system that presents the teeth in their normal appearance. Further, by positioning orthodontic brackets on the labial and buccal surfaces of the patient's teeth, the orthodontic brackets frequently cause irritation of the lip and mouth tissues of the patient. Moreover, the mere presence of orthodontic brackets between the teeth and lips or cheeks can interfere to some extent with muscle tone and develop undesirable speech characteristics. In some cases, a patient's teeth may tend to decalcify or become permanently discolored in the area covered by or adjacent to metal bands. Also, in many cases, the orthodontic appliances interfere with efficient oral hygiene and caries can develop on tooth surfaces that cannot be properly cleaned. Consequently, when the appliances are removed from the patient's teeth, the otherwise pleasant appearance of properly occluding teeth can be marred by irregular surfaces, band lines of discoloration and fissures that can be developed in the enamel. By locating the appliances on the lingual surfaces of the patient's teeth, the labial surface will remain clear of obstructions that otherwise would interfere with efficient oral hygiene. It is desirable, therefore, to provide for lingual edgewise orthodontic therapy because of the effective nature thereof and to allow the labial surfaces of the teeth of the patient to remain unobstructed to permit efficient cleaning thereof and to provide the patient with a pleasant facial appearance during the period of orthodontic therapy. It is also desirable to provide lingual edgewise orthodontic therapy without subjecting the patient to the presence of brackets and archwires between the teeth and lip and cheek surfaces.

In some cases, it is desirable that the orthodontist be capable of applying tooth movement forces to the lingual surfaces of a patient's teeth. With conventional edgewise therapy, forces are typically applied through brackets that are positioned only at the labial and buccal surfaces. It is desirable, therefore, to provide orthodontic brackets that permit edgewise therapy through location of orthodontic brackets at the lingual surfaces of the patient's teeth.

Single tie wing type brackets for edgewise therapy typically incorporate a base structure which is formed to define a precision active archwire slot which receives the rectangular edgewise archwire therein. Single brackets also incorporate a pair of tie wings that extend from the base and are positioned on opposite sides of the precision archwire slot. These tie wings are typically centered with respect to the bracket structure and are therefore intended to be positioned in substantially centered mesio-distal relation with the facial surface of the tooth to which the bracket is secured. A ligature wire or elastic is looped over each of the tie wings and is passed over the archwire, thus securing the archwire firmly in its precision slot.

Single brackets provide maximum efficiency in the application of tipping and torquing movements to teeth but are minimally efficient in rotational control. Initially, rotational control was accomplished by soldering or welding eyelets at the extreme mesial or distal portion of the band attached to the tooth. The orthodontist could ligate the eyelet to the archwire, pulling that surface closer to the archwire and causing the tooth to rotate about the centrally located bracket. This is a cumbersome and inefficient method of rotational control.

Subsequently, fixed or flexible rotation levers, projecting mesially and distally, were added to the centrally located single bracket. Thus, a rotated tooth would have the rotation wing projecting more facially than the bracket. The archwire would touch the rotation wing and, as the wire is ligated into the bracket, cause the tooth to rotate about the bracket. The rotation lever is adjustable to project more or less to the facial as desired. This permits the orthodontist to select the amount of rotation desired by adjusting the rotation lever rather than adjusting the archwire.

The disadvantage of the rotation lever is evident in the initial stages of treatment. The archwire will not touch the rotation lever if a tooth is tipped and rotated severely and will prevent either action from occurring unless the archwire is adjusted to strike the rotation lever when ligated. Thus, initial archwire insertion can be inefficient and require more expertise to ligate.

Twin brackets were introduced to alleviate the inefficient rotation effectiveness of the single bracket. Instead of one centrally located bracket, two brackets were placed at the mesial and distal portions of the tooth. Thus, when each bracket is ligated to the archwire, the facial surface will align itself with the archwire, rotating the tooth.

One of the principles of rotation in orthodontics is over-correction of the original problem to compensate for the rebound or relapse tendency. This is especially indicated for rotated teeth. Twin brackets do not have the capacity to over-rotate within themselves. For over-rotation with twin brackets, the archwire has to be bent or some auxilliary must be added to force the mesial or distal portion of the bracket away from the archwire. Further, single edgewise brackets, without rotation levers, are also lacking in over-rotation control capability which will be discussed in more detail hereinbelow.

One of the more important advantages of single brackets is the advantage that is afforded by the active length of archwire existing between the points of connection to adjacent brackets. This active archwire length is known in the industry as "interbracket width". Since the connecting point between adjacent single brackets is established at substantially the center of the adjacent teeth, the archwire length, and thus the interbracket width, extends to points near the centers of adjacent teeth. The lengthy archwire span that exists between single brackets allows lower magnitude forces to be applied to the teeth over longer periods of time as compared to circumstances where the interbracket width is limited and the active archwire span is short. The long span of archwire may be twisted much further without causing permanent yielding or deformation of the metal of the archwire. Where the archwire between brackets is of limited length, which is typical where twin brackets are employed with the edgewise technique, application of large magnitude forces to the teeth can occur with only minimal twisting or other deformation of the archwire. Thus, after limited movement of the teeth occurs, the forces induced by the archwire dissipate quickly, thereby requiring frequent adjustment in order to maintain optimum force application. Of course, it is evident that frequent adjustment of orthodontic appliances necessitates frequent visits by the patient for adjustment of the orthodontic appliance and is therefore disadvantageous to the patient in this regard. Such frequent adjustment also requires a significant amount of chair time in the office of the orthodontist, thereby either increasing the cost of treatment to the patient, or minimizing the commercial advantage of orthodontic treatment on the part of the orthodontist. It is desirable, therefore, to provide a system for orthodontic treatment wherein patient visits are minimized and chair time is also minimized, to the mutual benefit of both the patient and orthodontist.

Twin brackets for the edgewise technique have been employed for a considerable period of time. Twin brackets typically incorporate a pair of spaced projections that extend from or are formed by the bracket base, each projection being formed to define a precision active archwire slot segment. The spaced active archwire slot segments cooperate to define a precision archwire slot having the effect of extending the entire length of the base. Each of the projections is provided with gingival and occlusal tie wings, the tie wings terminating at the opposed side portions of the base structure. With the base structure centered in respect to the tooth being moved, the tie wings will be positioned in pairs at opposite sides of the tooth, thereby defining bracket structure with rotational control. The orthodontist may utilize ligature wires or elastic members between selected tie wings and the archwire to develop the force moments that are necessary for efficient rotational control.

One of the typical disadvantages in utilization of twin brackets is the consequent minimization of interbracket width that exists as the result of positioning the tie wings at opposed side portions of the bracket structure. Ordinarily, as explained above, minimization of interbracket width, in conjunction with the edgewise therapy, suffers the disadvantage of requiring frequent patient visits and increasing chair time because of the necessity for frequent adjustment of the appliance in order to maintain the force levels within the optimum range for efficient tooth movement. It is desirable, therefore, to provide lingual edgewise therapy with twin brackets having the interbracket width of single brackets, thus combining the desirable features of both single brackets and twin brackets.

Another significant disadvantage in the utilization of twin brackets is that the spaces that are typically available between the tie wings of adjacent brackets leave insufficient room between the teeth for closing loops and tie-back loops. It is desirable, therefore, to provide a lingual orthodontic appliance system that affords the advantages offered by twin brackets and yet provides ample space between certain tie wings of adjacent brackets to facilitate efficient use of closing loops and tie-back loops in conjunction with edgewise orthodontic therapy.

SUMMARY OF THE INVENTION

It is a principal feature of the present invention to provide a novel lingual orthodontic bracket system which permits utilization of edgewise orthodontic therapy at the lingual surfaces of the teeth.

It is also a feature of this invention to provide a novel lingual orthodontic appliance system which includes structure permitting application of efficient rotational control forces to the teeth of the patient.

It is an even further feature of this invention to provide a novel lingual orthodontic appliance system which allows the labial and buccal surfaces of the patient's teeth to remain free of orthodontic appliances, thereby permitting the normal relationship of the facial tissues and teeth to remain undisturbed and to provide the patient with a pleasant oral appearance during orthodontic therapy.

Among the several features of the present invention is contemplated the provision of a novel lingual orthodontic appliance system which enables mesial-occlusal insertion of an edgewise archwire into interfitting relation with the various orthodontic brackets of the anterior teeth, the cuspids, bicuspids and molars.

It is an even further feature of the present invention to provide a lingual orthodontic appliance system incorporating a specifically designed lingual tube that permits mesial-occlusal insertion of the end portions of an archwire therein and further permits rotation of the archwire in relation to the lingual tube to permit occlusal insertion of the archwire into the precision archwire slots of other brackets of the orthodontic appliance system.

It is another feature of this invention to provide a novel lingual orthodontic appliance system employing twin tie wings for effective rotational and tipping control and which also provides for maintenance of efficient interbracket spacing to permit efficient torquing movements in response to the edgewise technique.

It is also a feature of the present invention to provide a novel lingual orthodontic appliance system enabling an orthodontist to selectively utilize various combinations of rotation control, torque and tipping control simply through selection of various lingual edgewise brackets of single or twin form, at least some of which embody a centralized bracket section forming at least one precision active archwire slot in accordance with the principals of this invention.

It is an even further feature of this invention to provide a novel lingual orthodontic appliance system embodying combined features of single brackets and twin brackets and which system is of simple nature, is comparable with other orthodontic brackets from the standpoint of ease of installation and use and suffers no competitive disadvantage in comparison with other similar orthodontic bracket systems.

Briefly, the lingual orthodontic appliance system of the present invention incorporates a base structure which is adapted to be secured in immovable relation with a tooth. The base may be attached to bands that are positioned about the teeth and cemented in place or the base may be adapted for direct bonding to the tooth structure. The lingual base and bracket structure may take any one of several different forms within the spirit and scope of this invention, depending upon the teeth to which the brackets are to be secured. Regardless of the design of the particular brackets involved in lingual edgewise therapy, the archwire slots are oriented for occlusal insertion of the archwire therein.

For the anterior teeth the lingual brackets employ three tie wings in T-shaped orientation. Two spaced tie wings are positioned occlusally of the archwire slot while a single tie wing extends from the central portion of the bracket and gingivally of the archwire slot.

To provide for efficient rotation, the lingual brackets may be in the form of twin bracket structures having archwire relief between each of the pairs of tie wings and an intermediate bracket section that defines the precision archwire slot of the bracket. Thus, twin type lingual orthodontic brackets are provided which have maximum interbracket width such as is ordinarily afforded by single brackets for maintenance of maximum active archwire length between adjacent brackets. By providing an intermediate bracket section with pairs of tie wings at each extremity thereof and by providing archwire relief between each of the pairs of tie wings, a twin lingual bracket is provided having efficient rotational control. Further, since the intermediate bracket section of the bracket is machined to form an active archwire slot, the twin lingual brackets also incorporate the efficient tipping and torquing activity ordinarily achieved by single brackets. The resulting bracket is thus a combined single/twin bracket for lingual application and edgewise therapy.

Lingual brackets may also be provided of the single tie wing type as desired for particular teeth of the patient. The single tie wing lingual bracket forms an archwire slot that opens toward the occlusal and is extended to provide tie wings for ligating and pinning. The appliance system will include lingual tube brackets which are adapted for mesioocclusal insertion of the archwire ends into proper position therein. The terminal lingual attachments are designed to retain the tubular function thereof but are also of a configuration allowing mesioocclusal insertion of the archwire end portions therein to thus permit occlusal insertion of the arch portion of the archwire into the respective archwire slots of each of the other brackets. Each lingual tube is designed so that the archwire may be inserted in angular or in mesio-occlusal relation therewith. After having been inserted mesio-occlusally into the lingual tubes, the archwire is pivoted about pivot portions defined by the tubes to thus allow occlusal insertion of the arch portions of the archwire into properly seated relation within the archwire slots defined by the other brackets of the lingual appliance.

BRIEF DESCRIPTION OF THE DRAWINGS

In order that the manner in which the above recited advantages and features of this invention are attained and can be understood in detail, more particular description of the invention briefly summarized above may be had by reference to the specific embodiments thereof that are illustrated in the appended drawings, which drawings form a part of this specification. It is to be understood, however, that the appended drawings illustrate only typical embodiments of the invention and are, therefore, not to be considered limiting of its scope, for the invention may admit to other equally effective embodiments.

IN THE DRAWINGS

DETAILED DESCRIPTION OF PREFERRED EMBODIMENTS

In edgewise orthodontic therapy, the archwire, at least in finishing activities, is of rectangular cross-sectional configuration. In labial appliance installation the rectangular cross-sectional archwire is typically oriented with the parallel surface of greater dimension oriented substantially labially-lingually. The parallel edge surfaces of small dimension are generally oriented occlusally-gingivally. Hence, the edge of the archwire is oriented generally parallel with the labial surfaces of the teeth subject to angulation of the archwire slots to obtain interactive force transmission from the spring-like archwire, through the bracket structures to the teeth.

In accordance with the present invention, the term "edgewise" is intended to encompass archwires of any rectangular cross-sectional configuration including square. In cross-section, the archwire may be positioned with its greater dimension oriented either horizontally, i.e., labially-lingually, as in conventional edgewise appliances, or vertically, i.e., occusally-gingivally. For the most part, the present invention is discussed with the larger dimension of the archwire disposed vertically, i.e., occlusally-gingivally. Such is not intended to limit the spirit and scope of this invention in any manner whatever.

Figure 1:
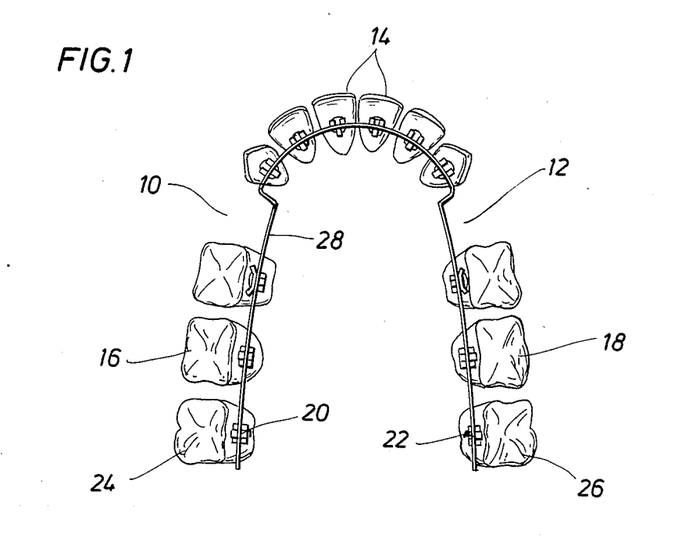
FIG. 1 is a pictoral representation in plan of the mandibular arch form and teeth of a patient undergoing orthodontic treatment and with a lingual edgewise orthodontic appliance constructed in accordance wtih the present invention being utilized during orthodontic treatment.

Referring now to the drawings and first to FIG. 1, there is shown the arch form of a patient's teeth while undergoing orthodontic therapy, it being understood that this particular arch form is only one representative example. In this case, teeth have been removed, such as at 10 and 12, and during orthodontic treatment, the space will be closed as the anterior teeth 14 are moved in the aleveolar arch toward the posterior teeth 16 and 18 including bicuspids and molars. Also shown in FIG. 1 is a lingual orthodontic appliance which is constructed in accordance with the present invention and includes lingual brackets of differing character for the anterior teeth 14, the bicuspids and the molars including molar tube brackets 20 and 22 for the last molars 24 and 26 which serve as anchors for the free extremity of the archwire 28. As is represented in FIG. 1, the various brackets of the lingual orthodontic system will be of differing constructing, depending upon the characteristics of the teeth to which the brackets are to be applied. Although the archwire 28 is shown to be of the offset variety, such is not intended to limit the spirit and scope of this invention, it being obvious that the archwire may be of the smoothly curved variety if desired for the character of treatment involved. The arch form of FIG. 1 is shown to be a mandibular arch. Both the maxilliary and mandibular arches will be provided with lingual orthodontic brackets to thus enable orthodontic treatment according to edgewise therapy.

Although lingual type orthodontic brackets have been developed for a significant period of time, their use has not been widespread because of certain undesirable characteristics. In the case of rather stiff edgewise arch wires, difficulty is often encountered in inserting the archwire end portions into lingual tube brackets, and yet being able to place the archwire within archwire slots of the various lingual brackets of the appliance. Archwire insertion is especially difficult if the teeth are excessively malposed. The present invention effectively facilitates simple and efficient insertion of the archwire end portions into the lingual tube brackets 20 and 22 of the molars 24 and 26. As will be explained in detail hereinbelow, the lingual tube brackets 20 and 22 are each adapted to receive the archwire extremities by mesio-occlusal insertion and provide the usual tube function as well as permitting occlusal insertion of the archwire into the archwire slots of other brackets of the orthodontic appliance system. Various aspects of the lingual appliance system of FIG. 1 are explained in detail in connection with FIGS. 2–15 hereinbelow. For the purpose of simplicity, the brackets are illustrated and described for bonded attachment to the lingual surfaces of the teeth. Such is not intended to limit this invention, however, since the brackets may be secured to bands which are cemented about the teeth or may be attached to the teeth by any other suitable means.

Figure 4:
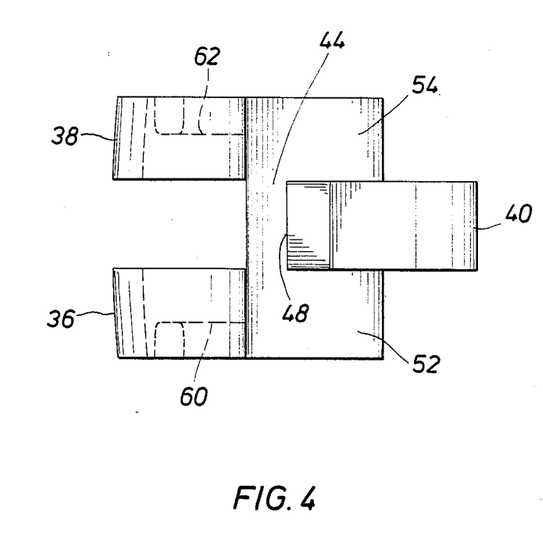
FIG. 4 is a plan view of the bracket structure of FIG. 2.
Figure 5:
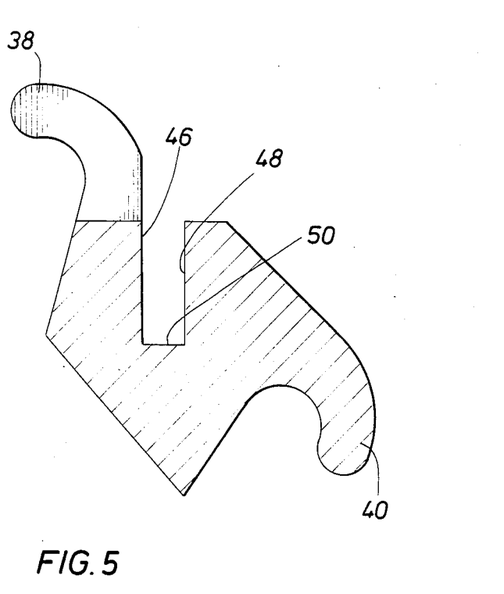
FIG. 5 is a sectional view of the bracket along line 5—5 of FIG. 3.

In view of the generally triangular configuration of the lingual surfaces of the anterior teeth, there typically is insufficient room for twin tie wing type lingual orthodontic brackets. For this reason, a bracket structure has been developed as shown in FIGS. 2–5 which is typically referred to as a T-bracket and which incorporates two occlusal tie wings on one side of the archwire slot and a single gingival tie wing at the opposite side of the archwire slot. The bracket nevertheless maintains the effect of a combination single/twin bracket having efficient interbracket width and defining a centralized edgewise archwire slot with archwire relief at each extremity thereof. The T-bracket construction, illustrated generally at 30, incorporates a body structure 32 defining an angulated attachment surface 34 which is oriented at an angle corresponding to the angle of the lingual surfaces of anterior teeth. Any suitable bonding medium may be employed to bond the bracket to the enamel lingual surface of a tooth. As shown in FIGS. 3, 4 and 5, the occlusal portion of the bracket body structure forms a pair of spaced tie wings 36 and 38 while a single tie wing 40 is formed by the gingival portion of the body structure. An edgewise archwire may be ligated to the bracket structure by means of ligature wire, ligature elastics or any other suitable means for securing the archwire to the bracket or applying force between the archwire and the bracket to achieve rotational movement of a tooth.

The body structure forms an intermediate bracket section 42 which is located at least partially between the spaced tie wing portions 36 and 38 having an extended portion which forms the single tie wing 40 of the bracket structure. An archwire slot 44 is defined by the intermediate bracket section and is formed by opposed parallel surfaces 46 and 48 together with a bottom surface 50. The surfaces 46 and 48 are spaced in precision manner in order that opposed parallel surfaces of an edgewise archwire may be retained in close fitting active relation in the archwire slot 44 for development of an active force transmitting relationship between the archwire and bracket.

It is desirable to provide a lingual orthodontic bracket for the edgewise technique that is basically in the form of a twin bracket structure which also incorporates single bracket-interbracket width in the rotational plane. In accordance with the present invention the archwire slot 44 is relieved at each side thereof by means of relief areas 52 and 54 on opposite sides of the single control tie wing 40 as shown in the elevational view of FIG. 2 and the plan view of FIG. 4. Thus the bottom wall 50 of the archwire slot includes extensions on either side of the slot defining side wall surface 48. This feature provides minimum effective width of the bracket for optimum interbracket width in the rotational plane. The intermediate bracket section and the relieved portions of the bracket structure at each extremity of the archwire slot cooperate to define a bracket structure having greater interbracket width than is ordinarily afforded by conventional twin orthodontic brackets. In fact, assuming the active archwire slot of the intermediate bracket section to be the same or less width as compared to the length of the archwire slot of a conventional single orthodontic bracket, the combination single/twin lingual bracket structure of FIGS. 2–5 therefore defines an interbracket width that is at least as great as the interbracket width defined by conventional single orthodontic brackets. As mentioned above, the length of the archwire span that exists between adjacent single orthodontic brackets alllows lower magnitude forces to be applied to the teeth over longer periods of time as compared to circumstances where the interbracket width is limited and the archwire span is short, such as is typical in the case of adjacent twin brackets of conventional nature. By providing the combination single/twin orthodontic brackets with an intermediate bracket section of limited width and with relieved areas between the adjacent pairs of tie wings, the free archwire span between the adjacent intermediate bracket sections of adjacent brackets will be as long as is ordinarily possible in edgewise orthodontic therapy. The long span of the archwire may therefore be twisted much further without causing permanent yielding or deformation of the metal from which the archwire is formed. In returning or springing back to its normal configuration, the edgewise archwire will therefore apply a tooth moving force to the tooth over a longer period of time as compared with conventional twin orthodontic brackets without adjustment of the orthodontic appliance. This feature, of course, minimizes the frequency of adjustment of the orthodontic appliance and thus significantly minimizes the amount of chair time and the frequency of visits that are required by the patient during the period of orthodontic therapy.

The intermediate bracket section of the combination single/twin lingual orthodontic bracket, together with the relieved tie wing portions of the bracket provide efficient rotational control, thus allowing the orthodontist to move the teeth rapidly to the final positions thereof and minimizing the treatment time necessary for effecting movement of the teeth to proper occlusion within the aleveolar arch.

In typical labial or lingual orthodontic brackets, the archwire is ligated to the bracket by wire or elastic members which extend under the tie wings and over the archwire. The ligature members apply a force between the archwire and bracket which helps to seat the archwire in the archwire slot. For the most part, edgewise archwires of rectangular cross-sectional configuration are significantly more stiff as compared to archwires of round cross-sectional configuration. Typically, the ligature members apply angulated forces to the archwire establishing a resultant force tending to force the archwire into the archwire slot. In many cases, the angle of force application between the ligature member and the archwire causes the resultant force acting on the archwire to be less than is needed to seat the archwire especially where the archwire is quite rigid. Accordingly, it is desirable to provide an orthodontic bracket structure which is designed to promote the application of significant force between the archwire and bracket, which force is directionally applied in more nearly aligned relation with the precision side walls of the archwire slots. The ligature member will then provide an enhanced, large magnitude force that maintains the archwire in positively seated relation within the archwire slot.

Figure 2:
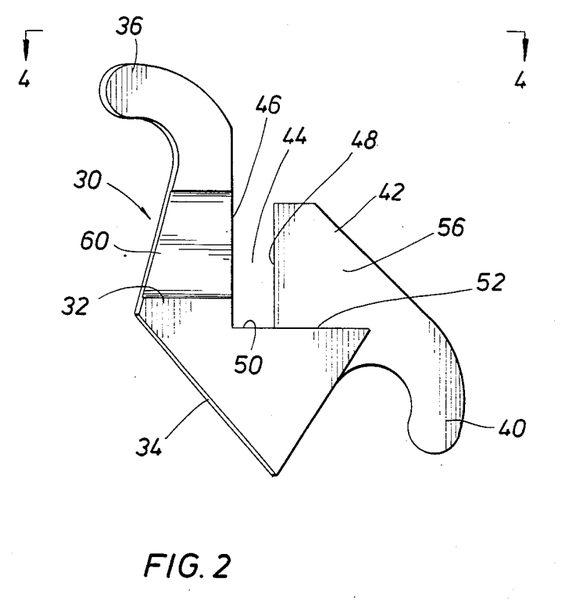
FIG. 2 is a side or proximal view of an edgewise lingual orthodontic bracket being a lower anterior bracket of the orthodontic appliance of FIG. 1.
Figure 3:
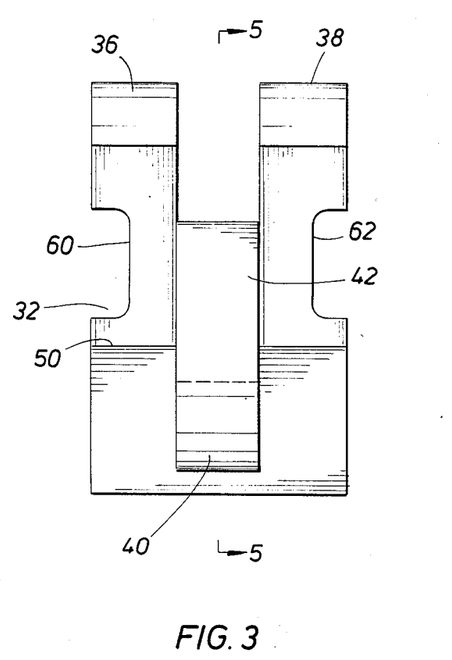
FIG. 3 is an elevational view of the bracket structure of FIG. 2 with the view directed toward the lingual.
Figure 6:
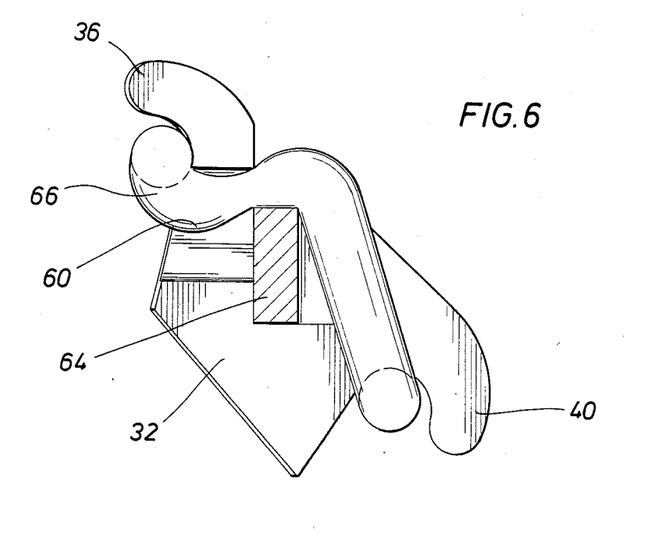
FIG. 6 is a view similar to that of FIG. 2 and showing a ligature element securing an edgewise archwire in firmly seated relation within the archwire slot of the bracket.

According to the present invention, as shown in FIGS. 2 and 3, the bracket base structure 32 is formed to define opposed ligature slots 60 and 62 which modify the structural configuration of a ligature member securing an edgewise archwire within the archwire slot. As shown in FIG. 6, an edgewise archwire 64 is retained within the archwire slot by a ligature member 66 which, in this case, is shown to be an elastic ligature member such as may be formed of rubber or any one of a number of suitable elastomeric materials. As shown, the ligature member 66 extends about the occlusal tie wings 36-38 and gingival tie wing 40 of an orthodontic bracket having the form shown in FIGS. 2-5. The ligature member 66 also extends through the opposed ligature slots 60-62 thereby causing it to bend sharply over the archwire 64 and thus apply forces as shown by the force arrows on the ligature member to the archwire as shown by the resultant force arrow on the archwire member. In this manner a conventional elastic ligature member is enabled to provide a materially enhanced seating force on the archwire 64 to thus maintain it in firmly seated relation within the archwire slot. Further, this materially enhanced resultant force functions to overcome the more rigid characteristics of an edgewise archwire to overcome its force resistance and seat it firmly within the archwire slot of the bracket.

Figure 7:
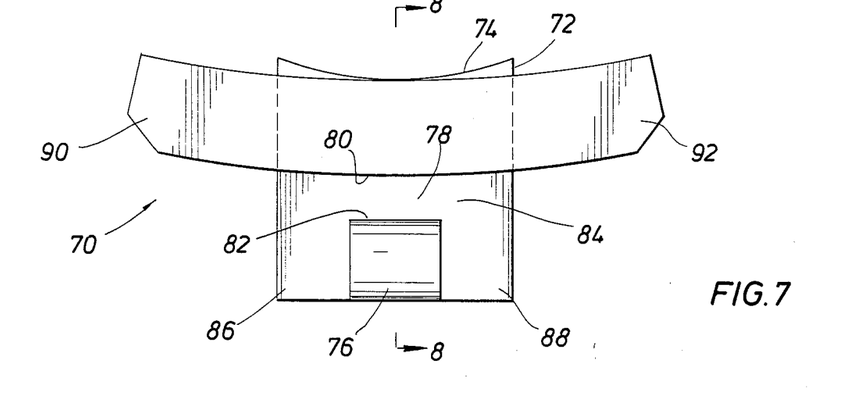
FIG. 7 is a plan view of a combination single/twin edgewise orthodontic bracket for lingual application to bicuspid teeth and representing another embodiment of the present invention.
Figure 8:
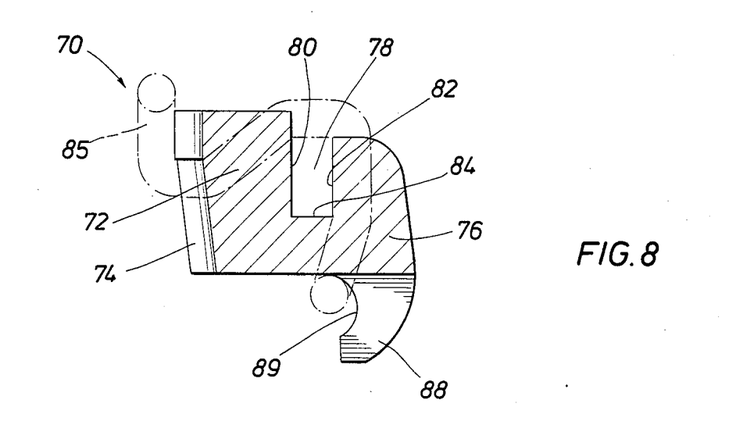
FIG. 8 is a sectional view taken along line 8—8 of FIG. 7 and showing an elastic ligature member securing an edgewise archwire within the archwire slot of the bracket.
Figure 9:
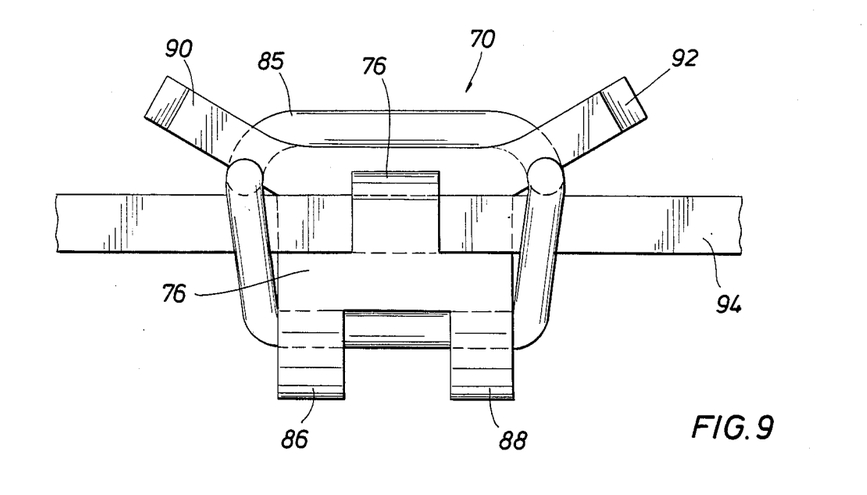
FIG. 9 is an elevational view of the orthodontic bracket of FIG. 7, also showing the elastic ligature member.

For application of the present invention to the posterior teeth such as bicuspids and molars, for example, the lingual bracket system may incorporate a bracket structure such as illustrated generally at 70 in FIGS. 7, 8 and 9. The bracket 70 is formed by a bracket base or body structure 72 forming a curved bonding surface 74 corresponding essentially to the curvature of the lingual tooth surfaces to which the bracket is to be attached. Any suitable bonding material may be utilized to establish firm retention of the bracket structure in assembly with posterior teeth. Alternatively, the bracket may be attached to a metal band which is cemented about the teeth.

The central section of the bracket base or body 72 forms a centrally located projection 76 forming an edgewise archwire slot 78 for receiving an archwire of rectangular cross-sectional configuration in close fitting, active, force-transmitting relation therein. The archwire slot is formed by opposed, parallel planar surfaces 80 and 82 and a planar bottom wall 84 which is positioned in substantially normal relation with the parallel surfaces 80 and 82. The bracket base also forms a pair of spaced gingival tie wings 86 and 88 positioned on opposite sides of the control tie wing 76. The spaced tie wings are undercut as shown as 89 in FIG. 8, forming hook-like tie wing structures enabled to receive a ligature element such as a wire or elastic member in retained relation therewith. The upper surfaces of the gingival tie wings are coplanar with the bottom wall surface 84 of the archwire slot to provide an extended bottom wall surface for efficient tipping control.

At the occlusal portion of the base structure 72 (the upper portion as shown in FIGS. 7, 8 and 9) the base structure forms a pair of opposed angulated tie wing projections 90 and 92 enabling ligature members to secure the edgewise archwire 94 within the centralized archwire slot 78 shown in FIG. 9. To secure the archwire, a ligature element 85 shown in broken line in FIG. 8 and full line in FIG. 9 will extend about the angulated tie wing projections 90 and 92, over the archwire 94 and through the undercut archwire slots or grooves 89 of the gingival tie wings 86 and 88. The ligature member is selectively positioned for force application between the archwire and bracket to achieve efficient archwire seating. During manufacture, the archwire projections 90 and 92 are formed in substantially coplanar relationship, parallel with the bottom wall surface 84 of the archwire slot. The projections are then bent approximately 30° to the angulated positions shown in FIG. 9.

Figure 10:
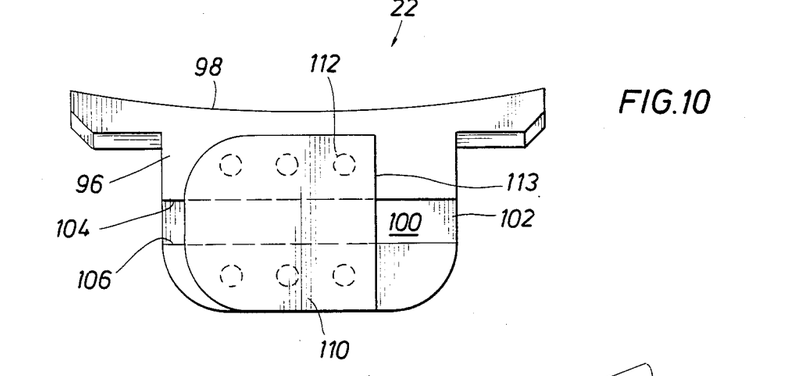
FIG. 10 is a plan view of a lingual tube orthodontic bracket for edgewise application which represents a portion of the orthodontic appliance set forth in FIG. 1.
Figure 11:
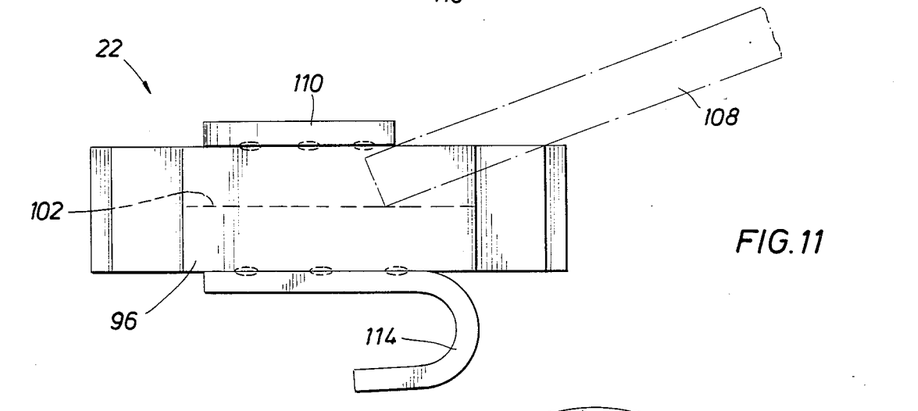
FIG. 11 is an elevational view of the lingual tube orthodontic bracket of FIG. 9.

Referring now to FIGS. 10 and 11, anchoring of the terminal end portions of the archwire is accomplished by means of molar tube brackets which are shown generally at 22 and which may be mounted on the lingual surfaces of the molars 24 and 26 by bonding as shown in FIG. 1 or by means of bands. For simplicity of manufacture and to reduce inventory requirements, the molar tube bracket incorporates a bracket base or body structure 96 forming a curved bonding surface 98 for bonded attachment of the base 96 to the enamel lingual surface of a molar. The bracket base forms an edgewise archwire slot 100 having a bottom wall surface 102 which is positioned in normal relation with a pair of spaced, parallel side wall surfaces 104 and 106. The bracket base is designed to apply torque forces to the molar which forces are transmitted from the archwire.

According to the present invention, it is desired that the edgewise archwire be capable of insertion into assembly with the orthodontic appliance system by way of pivotal movement about the terminal extremities thereof so as to bring the opposed sides and curved anterior portions thereof directly into the occlusally opening archwire slots of the various anterior and posterior brackets. To accomplish this feature, it is desirable that the end portions of the archwire have the capability of being inserted through the archwire slots of the lingual tubes with entry at least being initiated with the archwire in an angulated position such as shown in broken line at 108 in FIG. 11. To permit angulated insertion of the archwire 108 and to provide for development of a tubular archwire slot, a closure element 110 is secured to the body structure 96 such as by spot welding at a plurality of spot welding points 112. The closure plate 110 is cut away at 113 causing the archwire slot to be open at the archwire entry end thereof, thus permitting angulated positioning of the archwire. A gingival hook element 114 provides means for securing the archwire into the lingual tube to prevent mesial movement of the archwire after it has been firmly seated within the various archwire slots of the orthodontic appliance. The gingival hook element also provides for connection of inter and intra maxillary elastic members or tie back means to the molar, such as for space closure. The hook element is also spot welded or otherwise secured to the base member 96. As the archwire 108 is inserted into the archwire slots of the lingual tube brackets, it is positioned in angular fashion as shown in broken line in FIG. 11. Such positioning allows the ends of the archwire to slide along the surface 102 of archwire slot 100 to thus permit easy insertion of the archwire through the archwire slot. As the archwire is inserted, it is flexed to thereby allow the terminal portions of the archwire to be inserted fully through the enclosed archwires slots 100. The archwire is flexed toward the occlusal as the terminal ends are inserted into the molar tube brackets. After the archwire has been fully inserted into the archwire slots of the lingual tube brackets, the archwire is allowed to unflex and is brought into registry with the archwire slots of the various brackets by pivoting it toward the gingival by a pivotal seating movement. The archwire is then forced toward the gingival into fully seated relationship within the various occlusally opening archwire slots. The archwire is then ligated to the various brackets by means of elastic or metal ligature elements which extend about the various tie wings of the brackets.

Figure 12:
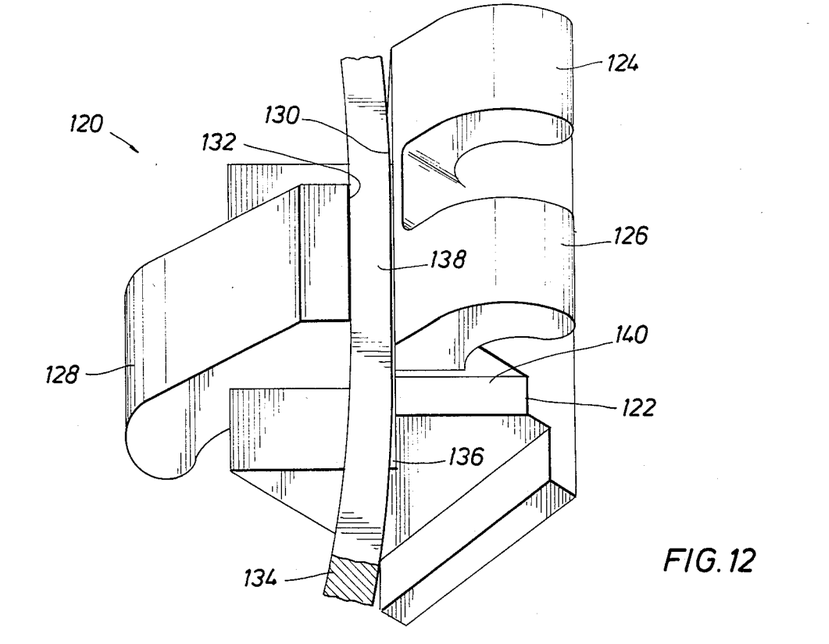
FIG. 12 is an isometric view of the lingual bracket of FIGS. 1–5 constructed in accordance with this invention and utilizing three tie wings in T-shaped orientation such as for application to anterior teeth.
Figure 13:
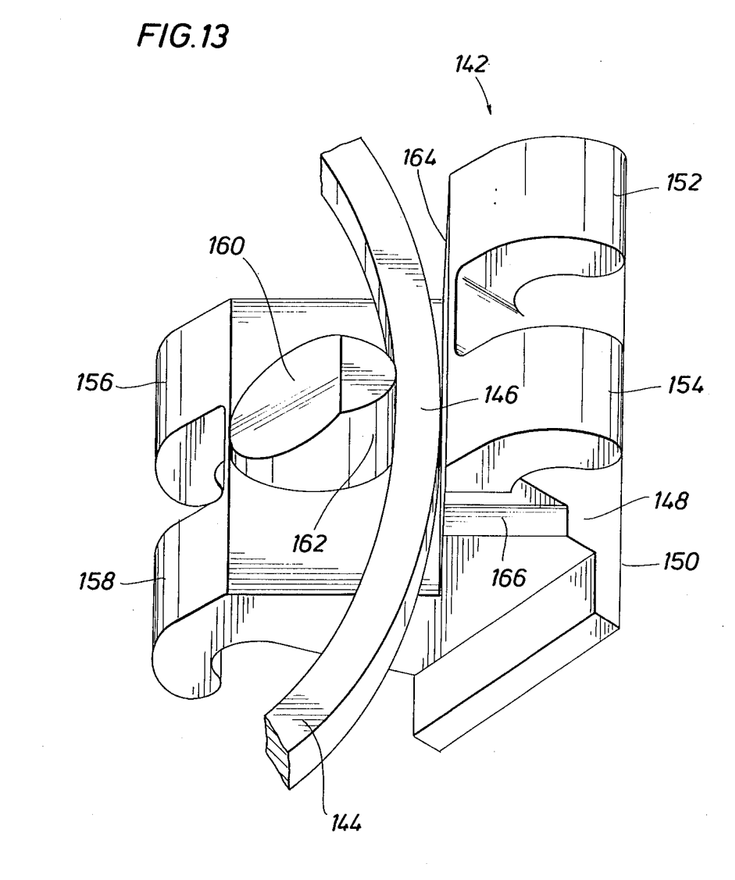
FIG. 13 is an isometric view of a twin lingual orthodontic bracket representing an alternative embodiment of this invention.
Figure 14:
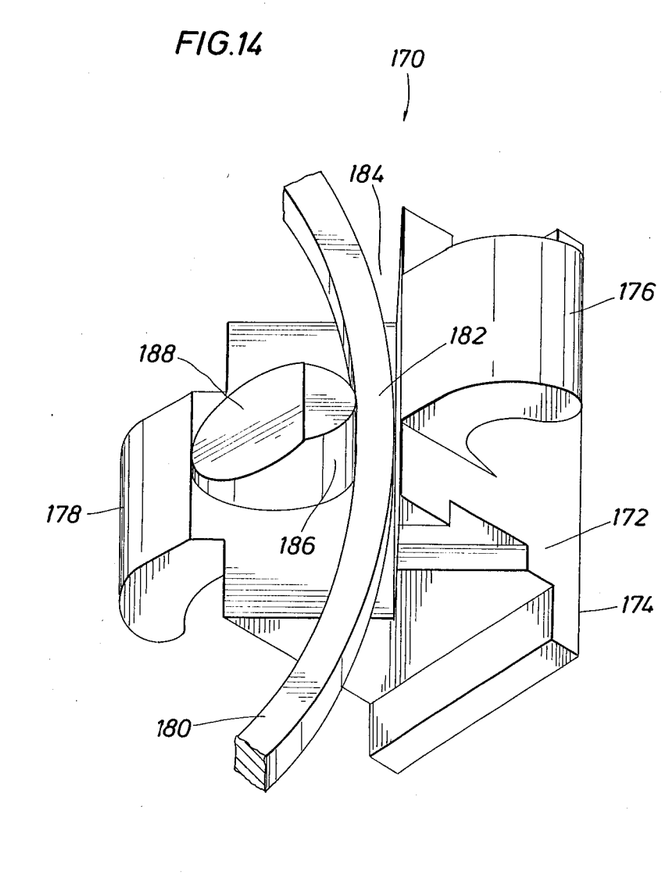
FIG. 14 is also an isometric view illustrating a lingual orthodontic bracket embodying this invention and utilizing single tie wings.

T-brackets for anterior teeth, twin brackets and single brackets may be provided according to the teachings of the present invention as shown in FIGS. 12, 13 and 14, respectively. As shown in the isometric illustration of FIG. 12, a T-type bracket is provided as shown generally at 120 for attachment to the anterior teeth of a patient. The T-bracket is of the form shown in FIGS. 2-5. The bracket 120 incorporates a bracket base or body 122 forming a pair of spaced occlusal tie wings 124 and 126. The central portion of the bracket forms a centralized gingival tie wing 128. To form the archwire slot of the bracket, the body structure 122 forms opposed parallel planar surfaces 130 and 132 which receive an edgewise archwire 134 therebetween The bottom surface 136 of the archwire slot extends beyond the extremities of the archwire slot for tipping control. To provide for adequate seating of the edgewise archwire within the archwire slot 138, the bracket base forms a pair of opposed ligature slots 140 similar to the ligature slots 60 and 62 of FIG. 3. A ligature member is therefore looped about the occlusal tie wings 124 and 126 through the ligature slot 140 and about the centralized tie wing 128. Thus, the ligature element bears upon the archwire and develops a resultant force tending to force the archwire into firmly seated and retained relation within the archwire slot.

As shown in FIG. 13, generally at 142, an edgewise bracket is provided for insertion of an edgewise archwire 144 into an archwire slot 146 which opens toward the occlusal. The bracket is defined by a base structure 148 having a bonding surface 150 for attachment of the bracket to the tooth structure. The base structure forms a pair of occlusal tie wings 152 and 154 which are disposed in spaced relation and a pair of gingival tie wings 156 and 158 which are similarly spaced. The central portion of the bracket structure forms a post element 160 forming a cylindrical surface 162 for essentially line contact with the archwire 144. The cylindrical surface is disposed in parallel, precision spaced relationship with a planar surface 164, thus defining the archwire slot. As in the case with the bracket structure shown in FIG. 12, provision of the post 162 provides the archwire 144 with efficient relief on either side of the relatively narrow archwire slot which is defined cooperatively by the post 160 and the planar surface 164. This feature allows the archwire 144 to have maximum interbracket width in each of the bracket constructions as shown in FIGS. 12, 13 and 14. In FIG. 14, a single orthodontic bracket is shown generally at 170 which is formed by a bracket base 172 defining a bonding surface 174. A single, centralized occlusal tie wing 176 and a single, centralized gingival tie wing 178 extend from the central portion of the body structure and provide for ligation of an edgewise archwire 180 within an archwire slot 182. The archwire slot is cooperatively formed by a curved surface 184 formed by the bracket base 172 and a cylindrical surface 186 formed by a post structure 188 extending from the central portion of the bracket body, the angular relationship of the bonding surface 174 and the parallel disposed surfaces 184 and 186 cause the archwire slot 182 to open toward the occlusal for occlusal insertion of the archwire 180 within the archwire slot. The single tie wing orthodontic bracket 170 is also formed for directionally oriented force application between the tie wings of the bracket and the ligature member to thus induce firm seating of the archwire 180 within the archwire slot 182.

In view of the foregoing, it is apparent that I have provided a lingual orthodontic appliance system which may be effectively utilized in accordance with the edgewise technique for efficient orthodontic therapy. Orthodontic therapy may be readily conducted while at the same time the labial and buccal surfaces of the teeth of the patient remain clear of appliance obstructions so that efficient cleaning may be readily conducted and oral hygiene may be more easily maintained. Moreover, the outward appearance of the teeth of the patient will be quite pleasant and the patient will not, therefore, be subject to the degree of psychological trauma ordinarily associated with application of orthodontic appliances to the labial surfaces of the teeth.

The lingual orthodontic appliances of the present invention are designed such that the edgewise archwire is inserted into the respective archwire slots by means of occlusal insertion since the archwire slots each open toward the occlusal even on the angulated surfaces of the anterior teeth. This feature effectively facilitates ease of installation of the archwire and ease of adjustments that are typically made during orthodontic therapy.

The various orthodontic brackets of the lingual appliance system of the present invention, with the exception of lingual tube brackets, each are provided with a central or intermediate active portion which forms an archwire slot opening toward the occlusal, which archwire slot is of the length ordinarily found in single tie wing type orthodontic brackets. This features promotes interbracket width of sufficient dimension to achieve substantial tooth movement between appliance adjustments. Further, the bracket design provides sufficiently for rotational characteristics, thereby providing an orthodontic appliance system which makes efficient use of the beneficial characteristics of both twin orthodontic brackets and single orthodontic brackets. The lingual orthodontic appliance system of this invention also incorporates molar tube brackets which allow mesio-occlusal insertion of the archwire therein and which provides a typical tube bracket function when the archwire is in operative relation therewith. It is therefore apparent that the present invention is one well adapted to attain all of the objects and features hereinabove set forth, together with other features which are inherent in the description of the apparatus itself.

While the foregoing is directed to the preferred embodiments of the present invention, other and further embodiments of this invention may be devised without departing from the basic concept thereof, and the scope of this invention is determined by the claims which follow.

I claim:

1. A lingual orthodontic bracket for edgewise orthodontic therapy of the teeth of the maxillary and mandibular arches, comprising:
   (a) base means for positioning at the lingual surface of a tooth and adapted to be disposed in fixed relation with said tooth, said base means defining proximal edges;
   (b) a centrally located archwire active section being defined by said base means and being of less mesial-distal width as compared to said base means, said archwire active section forming precision archwire slot means of the same mesial-distal length as said archwire active section and opening toward the occlusal for insertion of an edgewise archwire therein, said archwire slot means being formed by parallel active planar surfaces and a bottom surface disposed in substantially normal relation to said parallel active surfaces;
   (c) a pair of spaced tie wing elements being formed by said base means on one side of said archwire slot means and extending beyond said central archwire active section to the proximal edges of said base means;
   (d) a single tie wing element being defined by said base means on the opposite side of said archwire slot means and extending from said central archwire active section; and
   (e) said base means forming archwire relief areas extending from said precision archwire slot means to the proximal edges of said base means, whereby interbracket width between adjacent similar brackets is greater than the spacing of the base means thereof.

2. A lingual orthodontic bracket as recited in claim 1, wherein:
   said base means forms ligature orienting means at each proximal edge of said spaced tie wing means for directing a ligature element to apply force vectors in substantially aligned relation with the parallel active surface of said archwire to seat said archwire firmly in said archwire slot means.

3. A lingual orthodontic bracket as recited in claim 2, wherein said ligature orienting means comprise:
   mesio/distal slot means formed at each proximal edge of said bracket and directing said ligature member to bend sharply over said archwire.

4. A lingual orthodontic bracket as recited in claim 3, wherein:
   said mesio/distal slot means extends from a level slightly spaced toward the occlusal from the bottom surface of the archwire slot to a level spaced slightly toward the occlusal from said archwire.

5. A lingual orthodontic bracket as recited in claim 1, wherein:
   (a) said tie wings of said bracket are oriented in T-shaped manner with said pair of spaced tie wings projecting generally toward the occlusal from said base means and;
   (b) said single tie wing element projecting generally toward the gingival from said base means.

6. A lingual orthodontic bracket as recited in claim 5, wherein:
   said base means forms a pair of ligature slots at respective proximal edges of said spaced tie wings, said ligature slots receiving a ligature member and directing said ligature member to bend sharply over said archwire causing application of ligature force vectors to said archwire in substantially aligned relation with parallel active surface of said archwire slot means.

7. A lingual orthodontic bracket as recited in claim 1, wherein:
   said bottom surface of said archwire slot means extends beyond said archwire slot means toward the proximal edge of said base means and provides said bracket with efficient tipping control.

8. A lingual orthodontic bracket as recited in claim 7, wherein:
   one of said parallel active surfaces extends beyond said archwire slot means toward the proximal edges of said base means and provides said bracket with rotational control.

9. A lingual orthodontic bracket as recited in claim 1, wherein:
   said base means forms a centrally oriented projection of less mesial-distal width than that of said base means and extending away from the lingual, said centrally oriented projection forming one of said parallel active planar surfaces of said archwire slot means and also forming said single tie wing element.

10. A lingual orthodontic bracket for edgewise orthodontic therapy of the maxillary and mandibular arches, comprising:
   (a) base means for positioning at the lingual surface of a tooth;
   (b) a centrally located archwire active section being defined by said base means and being of less mesial-distal width as compared to said base means, said archwire active section forming precision archwire slot means opening toward the occlusal for insertion of an edgewise archwire therein, said archwire slot means being formed by parallel active planar surfaces and a bottom surface disposed in substantially normal relation to said parallel active surfaces;
   (c) a pair of spaced tie wing elements being formed by said base means on one side of said archwire slot means and extending beyond said central archwire active section to the proximal edges of said base means;
   (d) a second pair of spaced tie wings being defined by said base means on the opposite side of said archwire slot; and (e) said base means forming archwire relief areas extending from the ends of said archwire slot means to the proximal edges of said base means whereby interbracket width between adjacent similar brackets is greater than the spacing of the base means thereof.

11. A lingual orthodontic bracket as recited in claim 10, wherein:
said second pair of spaced tie wings project beyond said proximal edges of said base means.

12. A lingual orthodontic bracket as recited in claim 11, wherein:
said second pair of spaced tiw wings extend angularly toward the occlusal.

13. A lingual orthodontic bracket as recited in claim 10, wherein:
said base means forms a projection extending from said central bracket section toward the occlusal, said projection defining one of said parallel active planar surfaces.

14. A lingual orthodontic bracket as recited in claim 13, wherein:
the other of said parallel active planar surfaces extends beyond said archwire slot toward the proximal edges of said base means.

15. A lingual orthodontic bracket as recited in claim 13, wherein:
said bottom surface of said archwire slot means extends beyond said archwire slot means toward the proximal edges of said base means.

16. A lingual orthodontic bracket as recited in claim 15, wherein:
said pair of spaced tie wings form planar tie wing surfaces directed toward the occlusal, said planar tie wing surfaces being disposed in coplanar relation with said bottom surface of said archwire slot means.

17. A lingual orthodontic bracket as recited in claim 10, wherein:
said second pair of spaced tie wings are oriented to receive a ligature member such that said ligature member is bent sharply over said archwire causing application of force vectors to said archwire in substantially aligned relation with said parallel active surfaces of said archwire slot means.

18. A lingual orthodontic bracket for edgewise orthodontic therapy of the maxillary and mandibular arches, comprising:
(a) base means adapted for attachment to a tooth and for positioning at the lingual surface of the tooth, said base means forming one elongated archwire slot having parallel side surfaces and a bottom surface disposed in substantially normal relation with said parallel side surfaces, said archwire slot opening toward the occlusal; and
(b) a closure plate being attached to said base means at the occlusal surface portion thereof and forming a closure for said archwire slot, said closure plate terminating short of the length of said archwire slot permitting the mesial extremity of said archwire slot to be open toward the occlusal for initial mesio-occlusal insertion of the archwire end into said archwire slot.

19. A lingual orthodontic bracket as recited in claim 18, wherein:
said closure plate is connected to said base means by spot welding.

20. A lingual orthodontic bracket as recited in claim 18, wherein said lingual orthodontic bracket includes:
hook means extending from the gingival surface portion of said base means.

* * * * *